(12) United States Patent
Hansson

(10) Patent No.: US 6,503,252 B2
(45) Date of Patent: Jan. 7, 2003

(54) BONE SCREW, METHOD FOR PRODUCING THE THREADS THEREOF AND DRILL FOR DRILLING HOLES THEREFOR

(76) Inventor: Henrik Hansson, S-590 77, Vreta Kloster (SE)

(*) Notice: Subject to any disclaimer, the term of this patent is extended or adjusted under 35 U.S.C. 154(b) by 0 days.

(21) Appl. No.: 09/802,820

(22) Filed: Mar. 9, 2001

(65) Prior Publication Data

US 2002/0128657 A1 Sep. 12, 2002

(51) Int. Cl.[7] ............................................... A61B 17/86
(52) U.S. Cl. ........................... 606/73; 606/65; 606/69; 606/77; 411/115
(58) Field of Search ............................... 606/73, 71, 70, 606/72, 60, 65, 54, 57, 59, 232; 411/187, 389, 397, 395, 413, 415, 115, 307

(56) References Cited

U.S. PATENT DOCUMENTS

| | | | |
|---|---|---|---|
| 3,454,070 A | * | 7/1969 | Phipard, Jr. |
| 3,664,540 A | * | 5/1972 | Witkin |
| 5,242,447 A | * | 9/1993 | Borzone |
| 5,403,136 A | | 4/1995 | Mathys |
| 5,605,457 A | | 2/1997 | Bailey et al. |
| 5,695,497 A | * | 12/1997 | Stahelin |
| 5,730,744 A | * | 3/1998 | Justin et al. |
| 5,743,914 A | | 4/1998 | Skiba |
| 5,779,704 A | | 7/1998 | Kim |
| 5,964,768 A | * | 10/1999 | Huebner |
| 6,022,352 A | * | 2/2000 | Vanderville |
| 6,224,606 B1 | | 5/2001 | Horiuchi |

FOREIGN PATENT DOCUMENTS

| | | |
|---|---|---|
| DE | 29522089 | 9/1999 |
| EP | 0441577 | 8/1991 |
| EP | 0820731 | 1/1998 |

* cited by examiner

Primary Examiner—Pedro Philogene
(74) Attorney, Agent, or Firm—Tarolli, Sundheim, Covell, Tummino & Szabo L.L.P.

(57) ABSTRACT

The present invention relates to a bone screw, a method for producing the threads of the bone screw and a drill for drilling holes therefor. The bone screw is adapted for implants for fixation of bone fragments at fractures and it comprises a threaded or tapped part (16) which is adapted to be screwed into a bone fragment at the fracture. The threaded part (16) extends backwards from a front end portion (17) of the bone screw (6) to an untapped part (18) thereof and has threads (19) with the same outer diameter (YD). The threads (19) have the same pitch of thread (P) and extend from a core (21). At least front parts of the core (21) closest to the front end portion (17) of the bone screw (6) are conical and have their least diameter (MD) situated at the front end portion (17). The threads (19) have truncated crests (23) and the width (b1–b7) of the crests (23) of the threads (19) increases in backwards direction from the front end portion (17). The width (B1–B6) of grooves (20) between the threads (19) decreases in dependence of the increase in width (b1–b7) of the crests (23) (FIG. 2).

12 Claims, 6 Drawing Sheets

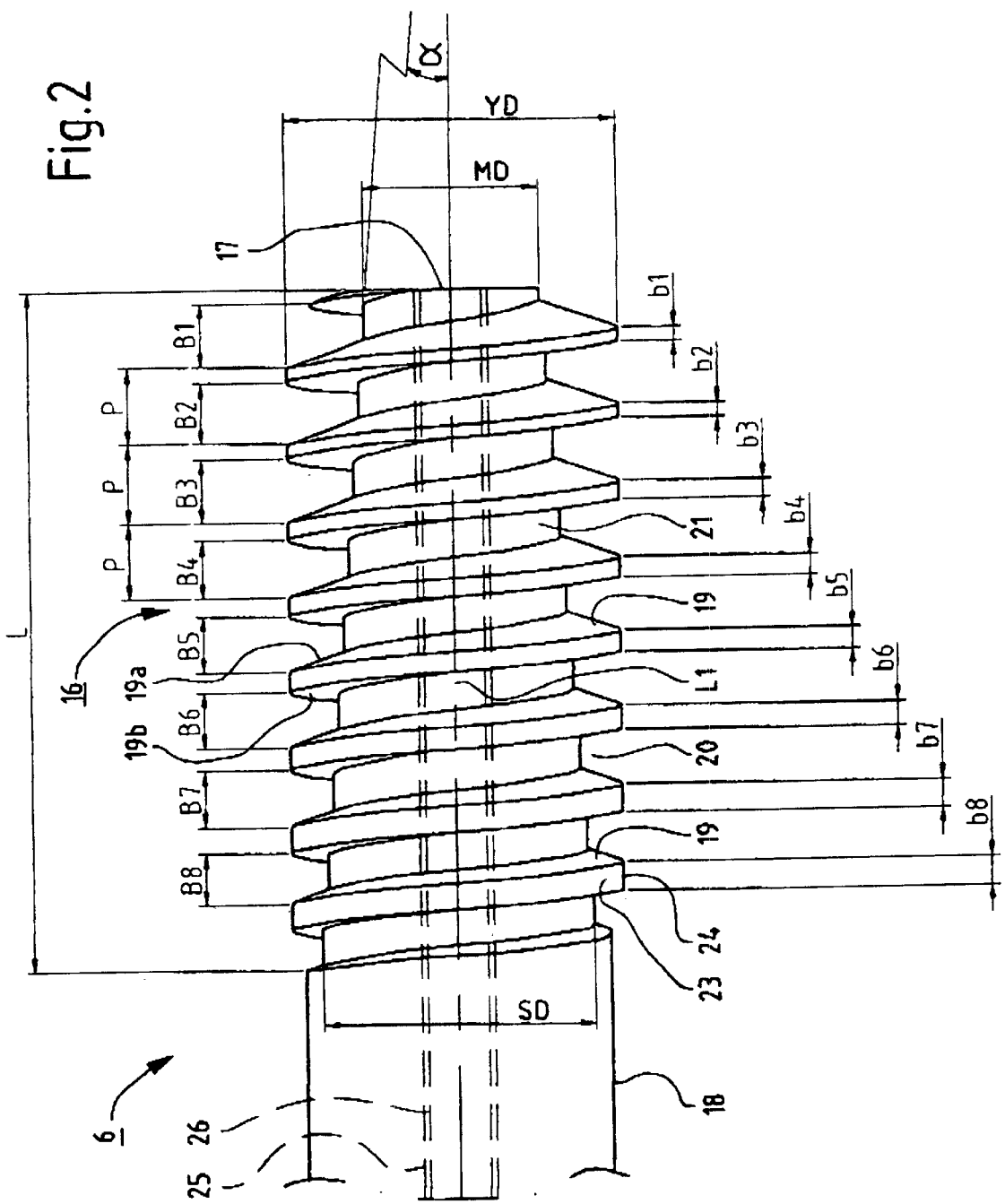

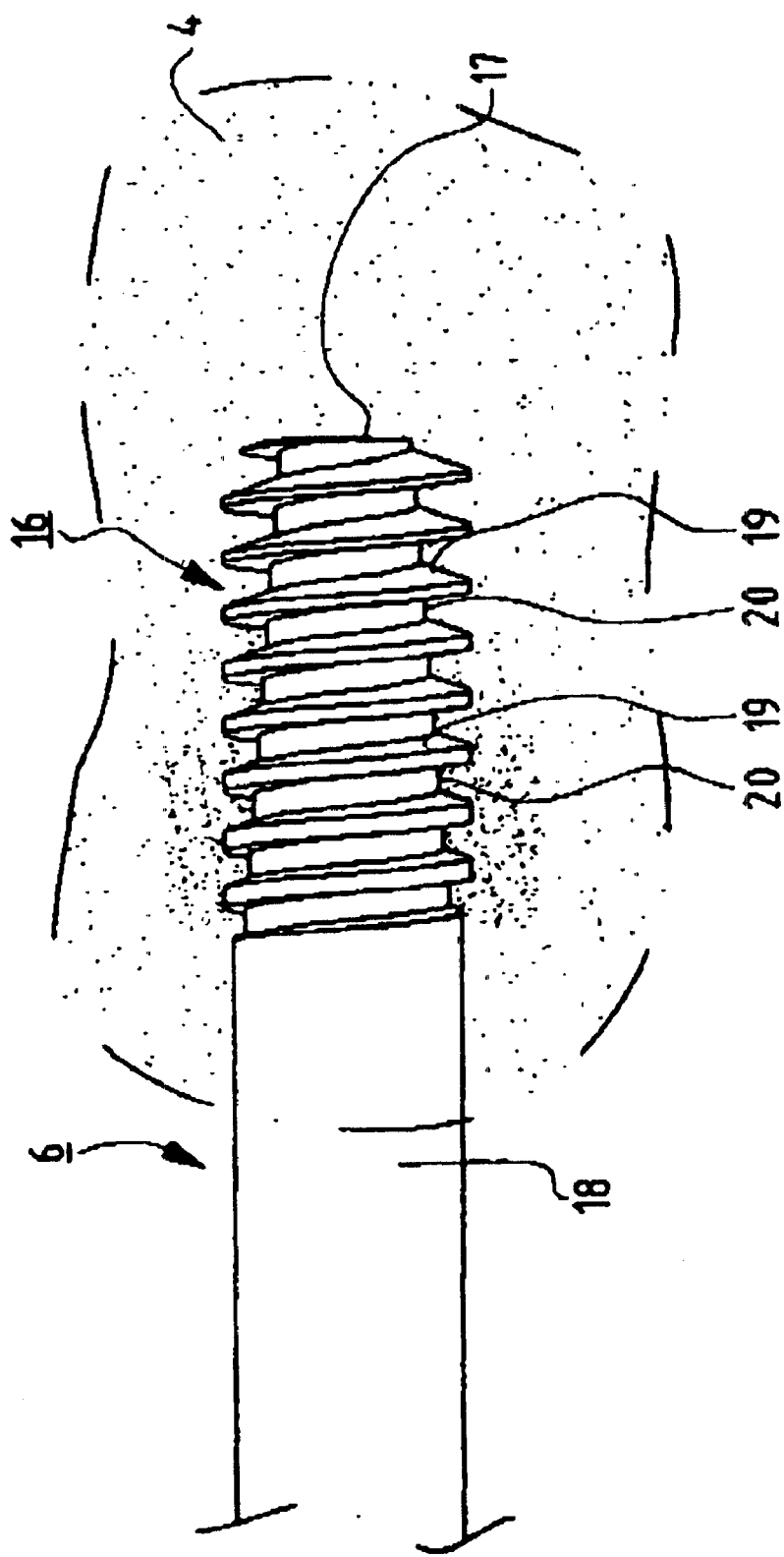

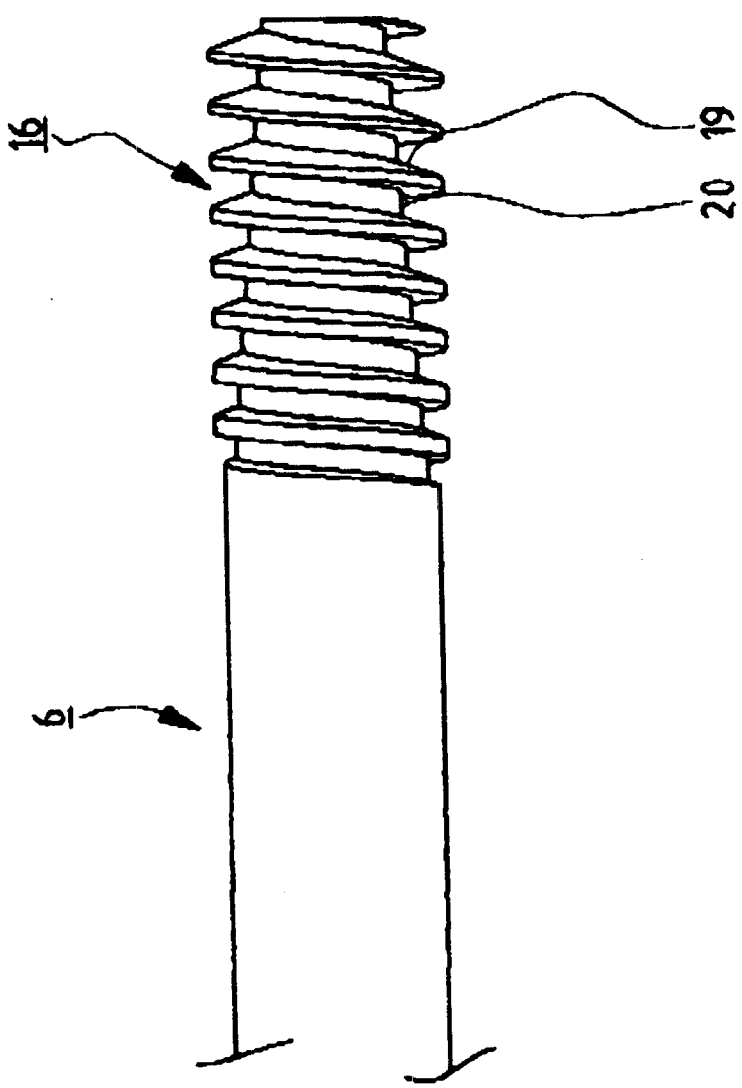

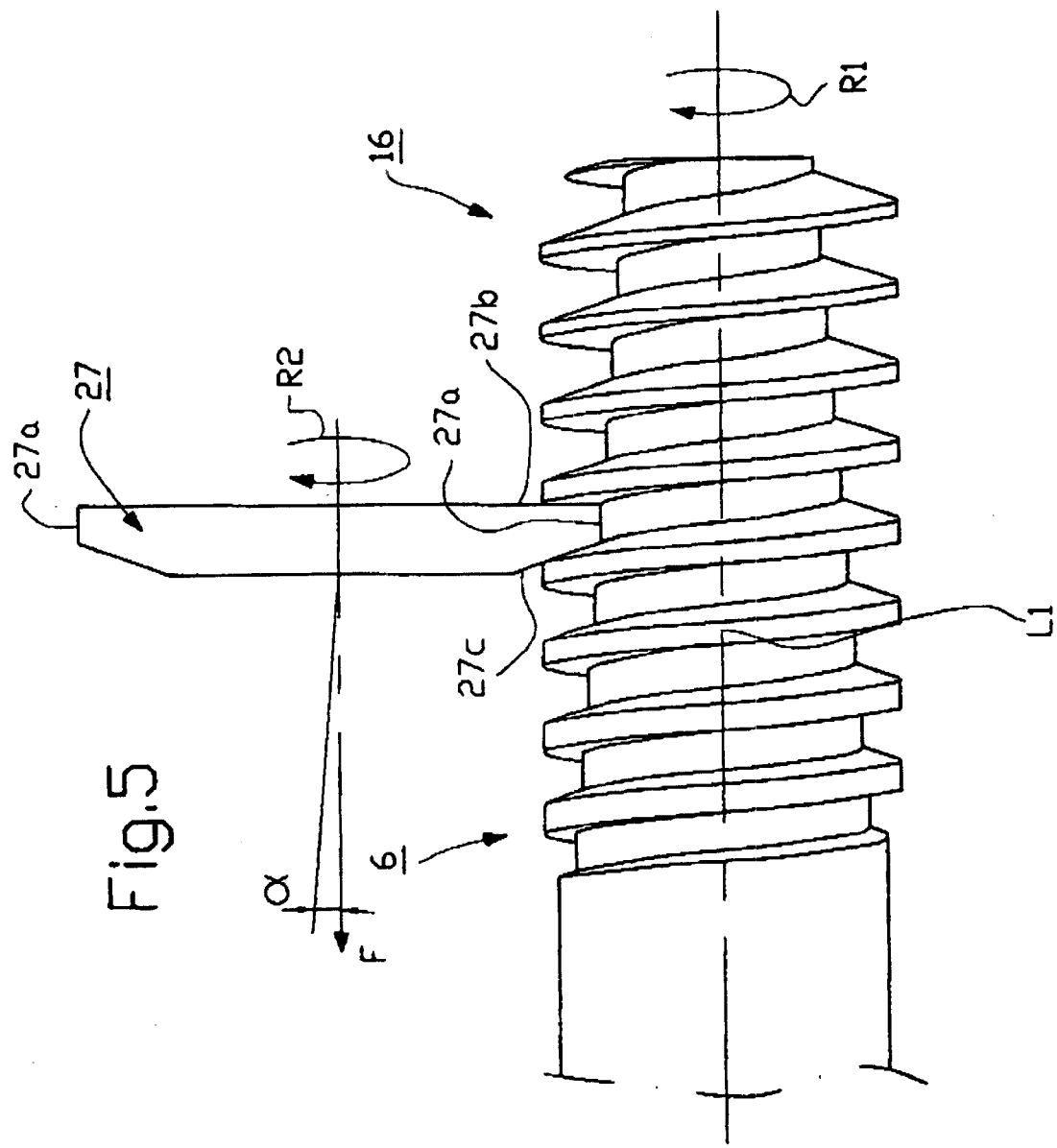

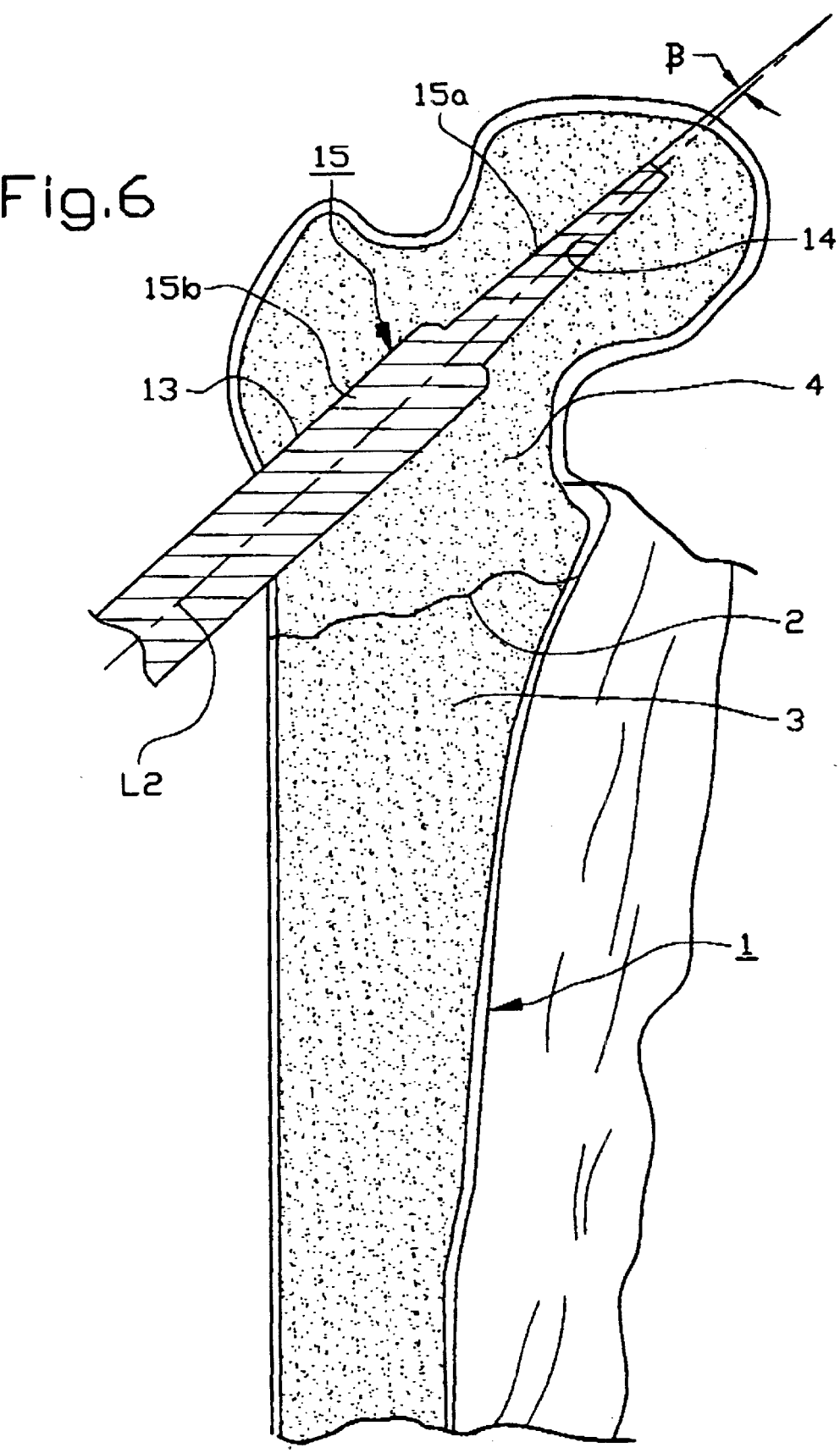

BONE SCREW, METHOD FOR PRODUCING THE THREADS THEREOF AND DRILL FOR DRILLING HOLES THEREFOR

The present invention relates to a bone screw for implants for fixation of bone fragments at fractures wherein the bone screw comprises a threaded or tapped part which is adapted to be screwed into a bone fragment at the fracture. The threaded part extends backwards from a front end portion of the bone screw to an untapped part thereof and has threads with the same outer diameter. The threads in the threaded part extend from a core and the threads of the threaded part have the same pitch of thread. The invention also relates to a method for producing the threads of the bone screw and a drill for drilling holes therefor.

Bone screws for bone implants (so called lag screws) for fixation of bone fragments at femoral fractures are previously known from e.g. U.S. Pat. No. 5,836,950. At such bone screws, the width of the grooves between the threads is the same along the entire part. This design is not optimal for stable anchoring to surrounding bone material, particularly not if said bone material is osteoporotic.

There are also prior art bone screws in which the threaded part has a cylindrical core. For being able to screw such a bone screw into bone material, one normally has to predrill said bone material for obtaining a hole therein for the cylindrical core or one has to use a special bone screw which at the front is provided with a drill bit for obtaining said hole.

At prior art bone screws, the threads are normally designed such that one has to cut threads in the bone material for the threads of the bone screw either by means of a separate thread tap or a thread tap which is built into the bone screw.

The object of the present invention has been to provide a bone screw with improved properties for engaging bone material particularly if this is osteoporotic and also in order to obviate predrilling of the bone material for the core if said bone material is osteoporotic. This is arrived at according to the invention by providing the bone screw with the characterizing features of subsequent claim 1.

The object of the invention is also a method for providing the threads of the bone screw and this method includes the characterizing measures of subsequent claim 17.

A further object is to provide a drill for use if one has to predrill the bone fragment for engagement by the bone screw. This is arrived at by providing the drill with the characterizing features of subsequent claim 18.

Since the core of the bone screw according to the characterizing features of claim 1 is conical, it can be screwed into spongy bone material without predrilling thereof for the core. Also, the conical core functions as a "plough" which presses the surrounding bone material in radially outwards direction, i.e. it compresses the bone material closest to the threaded part of the bone screw.

Since the bone screw according to said characterizing features of subsequent claim 1 further comprises a threaded part with threads having truncated crests, the width of which increases in backwards direction, i.e. with a thin thread at the front and thicker threads further backwards, it is possible to cut threads in the surrounding bone material directly with the threads of the bone screw instead of doing it with a separate thread tap or a thread tap built into the bone screw.

Since the width of the groves between the threads decreases because of the increase in width of the thread crests, it is achieved that the surrounding bone material is compressed by the threads when the bone screw is screwed into said bone material.

A further advantage with a conical core, that the threads are thin at the front and increase gradually in width and that the width of the grooves between the threads decreases, is that the bone screw gets a firm grip also in osteoporotic bone material when it is screwed into such bone material.

The invention will be further described below with reference to the accompanying drawings, in which FIG. 1 illustrates a bone screw according to the invention in cooperation with a bone implant which is shown partly in section and adapted for fixation of bone fragments at a femoral fracture;

FIG. 2 illustrates front parts of a bone screw according to the invention in a large scale;

FIG. 3 illustrates front parts of a bone screw according to FIG. 2 screwed into a bone fragment;

FIG. 4 illustrates front parts of a bone screw of the same type as in FIGS. 1–3, but with left-hand threads instead of right-hand threads;

FIG. 5 illustrates front parts of a bone screw according to FIGS. 1–3 and schematically a milling tool for milling the threads of the bone screw; and FIG. 6 illustrates a drill according to the invention in a bone fragment after drilling of a hole therein.

Figure 1:
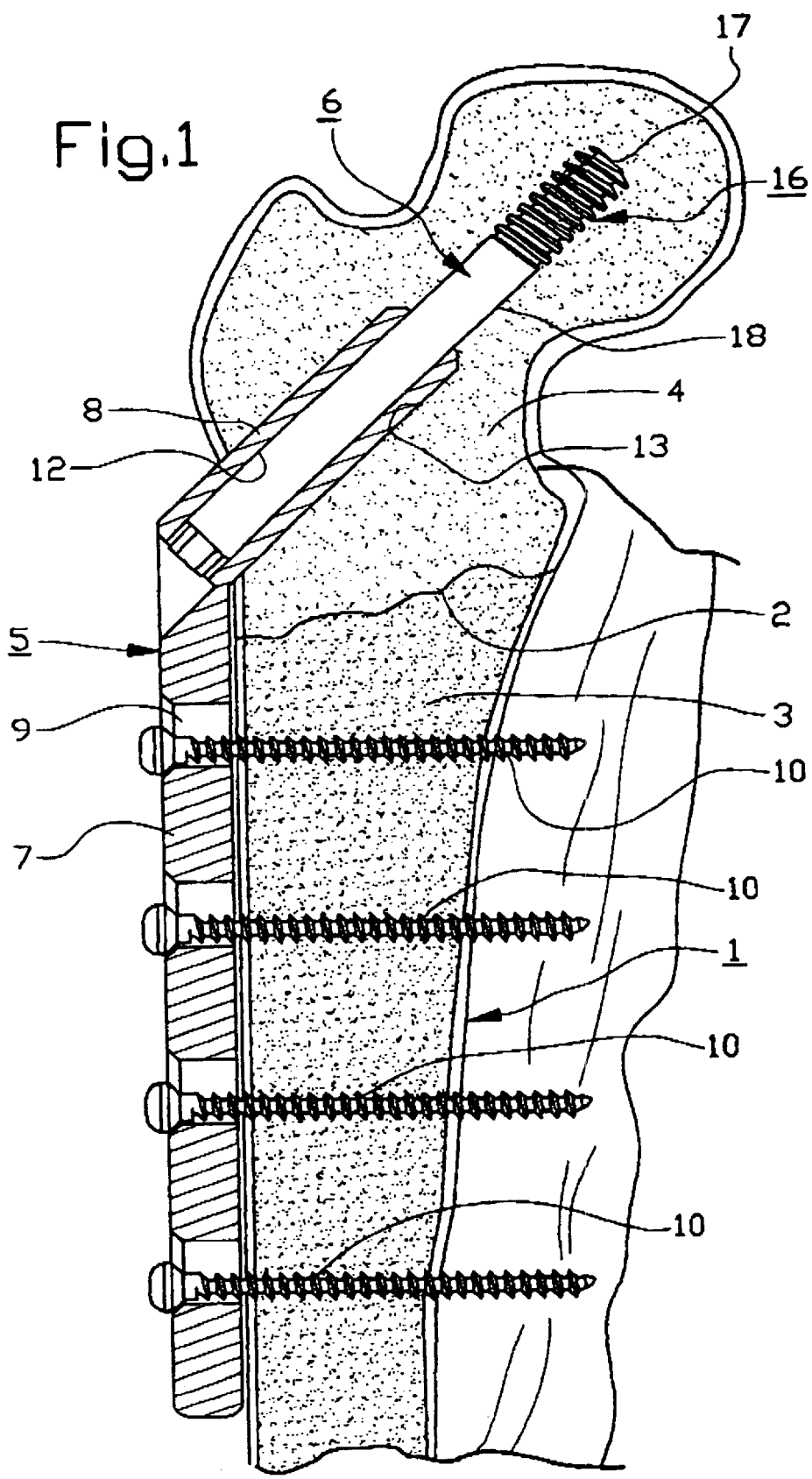

FIGS. 1 and 6 schematically illustrate a thighbone (femur), the femoral shaft 1 of which has a femoral fracture 2, more closely, in the illustrated example, a subtrochanteric fracture. The bone fragment 3 beneath the femoral fracture 2 includes substantial parts of the femoral shaft 1, while the bone fragment 4 above the femoral fracture 2 includes the femoral head. For fixation of the bone fragments 3, 4 relative to each other, various types of implants can be used, e.g. an implant 5 as illustrated in FIG. 1 and in connection therewith a bone screw 6 (so called lag screw) is used.

The implant 5 comprises a plate 7 or a corresponding member and a sleeve 8 or a corresponding member. The plate 7 has four or another suitable number of long holes 9 for screws 10 through which the plate 7 is attached or secured to the lower bone fragment 3. The long holes 9 are located and the screws 10 positioned therein such that the screws 10 and the lower bone fragment 3 can move in upwards direction towards the upper bone fragment 4. The sleeve 8 is inserted into a hole 13 in the upper bone fragment 4 and it has a hole 12 for the bone screw 6. which is secured to the upper bone fragment 4. The sleeve 8 can slide in its longitudinal direction relative to the bone screw 6 and said bone screw 6 as well as the sleeve 8 are in a manner known per se designed such that the bone screw 6 can not rotate relative to the sleeve 8 when it is inserted into said sleeve 8. Since embodiments for preventing said rotation are known, they have not been illustrated in the drawings. Eventually, there may be a stop screw (not shown) for preventing or limiting, when necessary, sliding of the sleeve 8 relative to the bone screw 6.

The hole 13 is predrilled by means of a drill 15. Eventually, the drill 15 may be a so called stepped drill with a rear portion 15b for drilling the hole 13 for the sleeve 8 and a front portion 15a for drilling a hole 14 for a core 21 of a threaded or tapped part 16 of the bone screw 6. It is however. not always necessary to drill the hole 14 since the threaded part 16 is designed to be screwed into the bone material if said bone material is osteoporotic.

Specifically, the method for application of the bone screw 6 normally starts with drilling, in a manner known per se, a thin hole (e.g. having a diameter of 3.2 mm) for a guide wire (not shown). Then, the thin hole is drilled into the hole 13 having a larger diameter for an untapped part 18 of the bone screw 6 and if the spongy parts of the bone material are not osteoporotic, the thin hole is drilled also into the hole 14 for the threaded part 16 but with a less diameter than the hole 13. If the bone material is osteoporotic, the inner portions of the thin hole is not drilled such that the hole 14 is formed. Said guide wire is removed when it is no longer needed.

The bone screw 6 has a front end portion 17 and its threaded part 16 extends backwards therefrom to the untapped part 18. The threaded part 16 comprises threads 19 and grooves 20 between the threads. The threads 19 have the same or substantially the same outer diameter YD along the threaded part 16.

The threads 19 extend from a core 21 having a circular cross section and extending along substantial parts of or preferably the entire length L of the threaded part 16. At least front parts of the core 21 are conical and the least diameter MD of the core 21 is situated front-most at the front end portion 17. The diameter of the core 21 increases gradually in backwards direction and it has its largest diameter SD at the transition 22 between the threaded part 16 and the untapped part 18. Each longitudinal side of the core 21 defines e.g. an angle of inclination $\alpha$ of 2–4° with the longitudinal axis L1 of the threaded part 16. At the bone screw 6 shown in the drawings, the angle $\alpha$ is 30°.

The shape of the core 21 can be conical along the entire or at least substantial parts of the length L of the threaded part 16, as is shown in the drawings. Another embodiment of the core 21 may be that it has a conical front part, a cylindrical part behind the conical front part and behind the cylindrical part another conical part which extends backwards to the untapped part 18 or terminates in its vicinity.

The threads 19 of the threaded part 16 have the same thread pitch P; the bone screw 6 illustrated in the drawings has e.g. a thread pitch of 3.2 at an outer diameter YD of 12.7 mm. The thread pitch of the bone screw 6 may e.g. be found within an interval of 3.0 at an outer diameter YD of 8.0 mm and 2.6 at an outer diameter of 6.5 mm. The bone screw with said latter pitch may be adapted for external fixation.

The threads 19 have truncated crests 23 with truncations 24 that are planar or have another shape. The width b1–b7 of these crests 23 increases in backwards direction from the front end portion 17. Preferably, the width b1–b7 of the crests increases gradually such that the crest 23 of the first thread 19 closest to the front end portion 17 is narrow, while the crests 23 of the following threads 19 in backwards direction become wider and wider.

Since the threads 19 have the same pitch P, the width B1–B6 of the grooves 20 between said threads will, in backwards direction, decrease because the width b1–b7 of the crests 23 increases.

This decrease or reduction of the width B1–B6 of the grooves 20 between the threads 19 means that a first groove 20 closest to the front end portion 17 will be the widest, while the width of the grooves behind will decrease, preferably gradually.

Preferably, all threads 19 in the threaded part 16 have crests with increasing width and preferably, all grooves 20 between the threads have a decreasing width.

Each thread 19 may have a front side which is inclined outwards/backwards relative to the front end portion 17 and the longitudinal axis L1 of the threaded part 16, and which defines or makes an angle of 70°±10% in relation thereto. Each thread 19 may also have a rear side which defines or makes an angle of 90°±5% in relation to the longitudinal axis L1. Hereby, the front sides 19a of the threads 19 become conical such that they facilitate screwing of the bone screw 6 into the bone material and their rear sides become transverse such that they can contribute to retain the bone screw 6 therein.

The width b1 of the narrowest crest 23 (on the thread 19 lying closest to the front end portion 17) can e.g. be 0.2 mm±10% and the width b7 of the widest crest 23 (on the thread 19 lying farthest away from the front end portion 17) can e.g. be 1.0 mm ±10%.

The width B1 of the widest groove 20 (closest to the front end portion 17) can e.g. be 2.5 mm±10% and the width B6 of the narrowest groove 20 (lying farthest away from the front end portion 17) can e.g. be 2.0 mm±10%.

An example of a bone screw 6 with the above design or similar designs can have the following dimensions:
1) the length L of the threaded part 16 lies within the interval 21–25 mm and is preferably 23 mm±5%;
2) there are 6–9, preferably 8 complete threads 19 in the threaded part 16; and
3) the threads 19 have an outer diameter YD lying within the interval 6–13 mm±10%, preferably 8 mm±5%.

The bone screw 6 may either be solid, i.e. lack holes for a guide wire or have a longitudinal hole 25 for a guide wire 26. Said latter embodiment is indicated with broken lines in FIG. 2.

There may be different bone screws 6 with the above or similar construction for the right as well as the left leg. For the right leg, these bone screws may have right-hand threads (e.g. FIG. 2), while they for the left leg may have left-hand threads (FIG. 4).

Hereby, one can improve the ability of the bone screw 6 not to unscrew itself from the bone material because of the influence thereon by forces in different directions depending on whether they are provided in the right or in the left leg.

A way to produce the threaded part 16 or threaded parts on bone screws of another type is to mill the grooves 20 between the threads 19 by means of a milling tool 27, as is schematically illustrated in FIG. 5, said milling tool 27 lacking milling surfaces for milling the crests of the threads 19, i.e. a milling tool 27 by means of which it is possible to mill grooves 20 having different depths between said threads 19.

By means of the milling tool 27, grooves 20 are milled which are deepest at the front end portion 17 of the bone screw 6 and the depth of which decreases in backwards direction from said front end portion 17 to form the conical core 21 in the threaded part 16.

The milling tool 27 is brought to cut the threads 19 with a uniform, regular pitch. Also, the milling tool is brought to provide threads 19 having truncated crests 23, the width b1–b7 of which increases in backwards direction from the front end portion 17. Furthermore, the milling tool 27 is brought to provide grooves 20 between the threads 19, said grooves having a width B1–B6 which decreases in said backwards direction depending on the increase in width b1–b7 of the truncated crests 23.

The milling tool 27 has three milling surfaces, namely one milling surface 27a for milling the bottom of the grooves 20 between the threads 19, one milling surface 27b for the rear sides 19b of the threads 19 and one milling surface 27c for the front sides 19b of the threads 19.

During milling, the bone screw 6 rotates in the direction of rotation Rl and the milling tool 27 in the direction of rotation R2. The motion pattern in operation during milling may vary. Thus, the milling tool 27 can be moved substantially in an axial direction of movement F relative to the bone screw 6 or the bone screw 6 may eventually be moved in substantially the corresponding direction relative to the milling tool 27. For milling grooves 20 having different depths, the milling tool 27 can be moved in a sideways direction with an angle $\alpha$ relative to the bone screw 6 or the opposite, i.e. the angle α the longitudinal sides of the core 21 is making or defining with the longitudinal axis L1 of the threaded part 16.

In the embodiment shown, the threads of the bone screw 6 have a larger outer diameter YD than the untapped part 18 thereof. However, the outer diameter YD of the threads may be equal to the outer diameter of the untapped part, particularly if the bone screw shall be used in connection with intramedullary nails.

The front portion 15a of the drill 15 is preferably conical for drilling a conical hole 14 for the conical core 21 of the bone screw 6. The angle of inclination β between longitudinal lateral parts of the front portion 15a and the longitudinal axis L2 thereof corresponds with the angle of inclination α between the longitudinal lateral parts of the core 21 and the longitudinal axis L1 of the threaded part 16.

The invention is not limited to the embodiment of the bone screw or the drill described above and illustrated in the drawings, nor to the method for producing threads described above, but said embodiments and said method may vary within the scope of the subsequent claims.

It should also be mentioned that the bone screw 6 can be used at other fractures than trochanteric femoral fractures, such as humerus fractures, and it can be used at completely different bone implants than the one described and illustrated, e.g. at implants for external fixation.

What is claimed is:

1. Bone screw for implants for fixation of bone fragments at fractures, wherein the bone screw (6) comprises a threaded part (16) which is adapted to be screwed into a bone fragment (4) at the fracture (2), the threaded part (16) extends backwards from a front end (17) of the bone screw (6) to an unthreaded part (18) thereof, the threaded part (16) has threads (19) with the same outer diameter (YD) throughout the extent of said threaded part (16), the threads (19) in the threaded part (16) have the same pitch of thread (P) throughout the extent of said threaded part (16), the threads (19) on the threaded part (16) extend from a core (21), the core (21) has a uniform taper throughout the length of the threaded part (16) and has a smallest diameter (MD) situated at said front end (17) of the bone screw (6), the threads (19) have truncated crests (23), that the width (b1–b7) of the crests (23) of the threads (19) increases in a backwards direction from the front end (17) of the bone screw (6), the width (B1–B6) of groove (20) between the threads (19) decreases in a backward direction from the front end (17) of the bone screw (6) as the width (b1–b7) of the crests (23) increases.

2. Bone screw according to claim 1 wherein the width (b1–b7) of the crests (23) of the threads (19) increases gradually in backwards direction from the front end (17) of the bone screw, and that the width (B1–B6) of the groove (20) between the threads (19) decreases gradually in backwards direction from the front end (17) of the bone screw.

3. Bone screw according to claim 1, wherein each thread (19) has a front side (19a) which is inclined outwards and backwards relative to the longitudinal axis (L1) of the threaded part (16) and which makes an angle of 70°±10% in relation to the longitudinal axis (L1), and that each thread (19) has a rear side (19b) which makes an angle of 90°±5% relative to said longitudinal axis (L1).

4. Bone screw according to claim 1, wherein the thread pitch (P) of the threads (19) lies within an interval of 3.2 at an outer diameter (YD) of the threads (19) of 12.7 mm at 2.6 at an outer diameter (YD) of 6.5 mm, and that the thread pitch (P) is 3.2 at an outer diameter (YD) of 12.7 mm±10%.

5. Bone screw according to claim 1, wherein the width (b1) of the narrowest crest (23) is 0.2 mm±10% while the width (b7) of the widest crest (23) is 1.0 mm±10%, and that the width (B1) of the widest groove (20) between the threads (19) is 2.5 mm±10% while the width (B6) of the narrowest groove (20) is 2.0 mm±10%.

6. Bone screw according to claim 1, wherein a longitudinal side of the core (21) forms an angle of inclination (a) of 2–4°±10%, with the longitudinal axis (L1) of the threaded part (16).

7. Bone screw according to claim 1, wherein there are 6–9 complete threads (19) in the threaded part (16), and that the threads (19) have an outer diameter of 6–13 mm±10%.

8. Bone screw according to claim 1, wherein the threaded part (16) is solid in such a manner that there is no through hole for a guide wire in the threaded part.

9. Bone screw according to claim 1, wherein the threaded part (16) has a through hole (25) for a guide wire (26) in the threaded part.

10. Bone screw according to claim 1, wherein the bone screw (6) is connectable to a bone implant (5) such that after connection the bone screw can be rotated in relation to the bone implant.

11. Bone screw according to claim 10, wherein the bone screw (6) is designed to fit into a sleeve (8) on the implant (5), said sleeve (8) being adapted for insertion into a hole (11) provided in a bone fragment (4) on one side of the fracture (2) and said sleeve (8) being connected to a plate (7) with holes (9) for screws (10) for securing the plate (7) to a bone fragment (3) on the other side of the fracture (2).

12. Bone screw according to claim 1, wherein the bone screw (6) for fixation of bone fragments (3, 4) at femoral fractures (2) on a right leg has right-hand threads, and the bone screw (6) for fixation of bone fragments (3, 4) at femoral fractures (2) on a left leg has left-hand threads.

* * * * *